(12) United States Patent
McConnell

(10) Patent No.: US 9,844,497 B2
(45) Date of Patent: Dec. 19, 2017

(54) WIPE WARMER AND HUMIDIFYING DEVICE THEREOF

(71) Applicant: Thomas E. McConnell, Santa Ynez, CA (US)

(72) Inventor: Thomas E. McConnell, Santa Ynez, CA (US)

(*) Notice: Subject to any disclaimer, the term of this patent is extended or adjusted under 35 U.S.C. 154(b) by 361 days.

(21) Appl. No.: 14/642,729

(22) Filed: Mar. 9, 2015

(65) Prior Publication Data

US 2016/0265788 A1 Sep. 15, 2016

(51) Int. Cl.
*A61K 8/02* (2006.01)
*A47K 10/42* (2006.01)
*A47K 10/32* (2006.01)

(52) U.S. Cl.
CPC .......... *A61K 8/0208* (2013.01); *A47K 10/421* (2013.01); *A47K 2010/3273* (2013.01); *A47K 2010/3293* (2013.01)

(58) Field of Classification Search
CPC ........ F24C 15/003; A61K 8/0208; A61F 7/02; A47K 10/16; A47K 10/32; A47K 10/42; A47K 10/24; A47K 10/28; A47K 2010/3273; A47K 2010/3293
USPC ...................................................... 219/401
See application file for complete search history.

(56) References Cited

U.S. PATENT DOCUMENTS

| 2,443,321 | A | | 6/1948 | Miner, Jr. |
| 4,084,080 | A | * | 4/1978 | McMahan ............. A45D 44/00 122/459 |
| 4,762,113 | A | | 8/1988 | Hamasaki |
| 5,397,875 | A | * | 3/1995 | Bechtold, Jr. .......... A45C 15/00 132/315 |
| 6,639,185 | B1 | | 10/2003 | McConnell et al. |
| 6,674,048 | B2 | | 1/2004 | McConnell et al. |
| 7,094,992 | B1 | | 8/2006 | Wray et al. |
| 8,044,325 | B1 | | 10/2011 | Cooper |
| 2011/0192830 | A1 | * | 8/2011 | Wilson ...................... F24C 7/10 219/386 |

FOREIGN PATENT DOCUMENTS

| CN | 2506190 Y | 8/2002 |
| CN | 2681664 Y | 3/2005 |
| CN | 202458157 U | 10/2012 |
| TW | 128199 | 2/1990 |
| TW | 510786 | 11/2002 |
| TW | M333901 | 6/2008 |

* cited by examiner

*Primary Examiner* — Brian Jennison
(74) *Attorney, Agent, or Firm* — WPAT, P.C., Intellectual Property Attorneys; Anthony King

(57) ABSTRACT

A wipe warmer having a container to receive liquid and sponge pad therein, where the container is placed under the wipes to keep the wipes moist. The container has a top and a support plate within, both of which are perforated allowing moisture to pass through. These perforations offset each other to facilitate efficient saturation of the sponge pad, when the sponge pad is placed between the perforated top and the perforated plate. Further, the container can be a removable basket-like structure. Alternatively, all or part of the container can be an integral part of the wipe warmer. While the wipes can be placed on top of the container, an alternative design is to place the wipes and the container side-by-side.

18 Claims, 6 Drawing Sheets

WIPE WARMER AND HUMIDIFYING DEVICE THEREOF

BACKGROUND OF THE INVENTION (1) Field of the Invention

The field of the invention is for a wipe warmer for heating and humidifying wipes therein, and more particularly relates to a humidifying device placed within a wipe warmer to prevent excessive drying or yellowing of the wipes therein.

(2) Description of Related Art Including Information Disclosed Under 37 CFR 1.97 and 1.98

Various wipe warmers are known for keeping baby wipes in a warm environment, so as to provide deeper cleaning and to reduce irritation to baby's skin caused by cold wipes. However, most of these wipe warmers fail in maintaining appropriate wetness of the baby wipes over a prolonged period of time (baby wipes may dry and discolor). Although some conventional wipe warmers are designed to be used with a wetting pad/sponge for the purposes of preventing baby wipes from dehydrating and discoloring, there remains a need for better and longer lasting ways to keep baby wipes wet.

For example, China Patent No. 01278643.8 (which is herein incorporated by reference in its entirety) discloses a conventional wipe warmer having a thermal tank for heating water therein, a tray positioned above the thermal tank for bearing baby wipes, and a net formed between the thermal tank and the tray. In operation, the net is also heated when the thermal tank heats the water, thus stabilizing the air temperature in the inner room as defined by the thermal tank and the tray. Accordingly, warm vapor with stable temperature is introduced to the baby wipes via through holes of the tray. However, in practical use, the heated net adjacent to the tray may cause the lower baby wipes to dry up faster, thus decreasing the effectiveness of the warm vapor.

Furthermore, Applicant's own U.S. Pat. No. 6,674,048 8 (herein incorporated by reference in its entirety) discloses a conventional wipe warmer also having a thermal tank for heating water therein and a tray positioned above the thermal tank for bearing baby wipes. This conventional wipe warmer further includes a sponge disposed on the bottom of the thermal tank to support the tray. Since this sponge is soaked in the water and disposed between the thermal tank and the tray, it may serve as a thermal buffer between them, thus decreasing heating effect to the baby wipes. Moreover, while naturally formed pores of the sponge pad can serve as passage ways for warm vapor, a sponge directly in contact with the bottom of the thermal tank over an extended period of time may be damaged by heat.

As a result, there is still a need for improving wipe warmers so as to largely minimize drying and discoloration of on baby wipes received therein.

BRIEF SUMMARY OF THE INVENTION

The inventive subject matter addresses and overcomes the above-described drawbacks of conventional wipe warmers by (either portably or non-portably) providing a humidifying device for supporting a liquid reservoir (e.g., wetting pad, sponge) spaced apart from an area that holds liquid (e.g., water).

Among the many different possibilities contemplated, the wipe warmer of the inventive subject matter may have a portable/removable container having a bottom and adapted to receive liquid above the bottom (i.e., an area that holds liquid). This container has a partitioner coupled with the container to form and/or enclose an inner area in the container. In one specific embodiment, this partitioner is a pivoting lid to the container. Generally the partitioner has a first surface facing the inner area, a second surface opposite to the first surface and adapted to face a wipe-receiving area, wherein the wipe-receiving area is adapted to receive at least one wipe. In yet another specific embodiment, wipes are stacked directly on top of the partitioner.

Generally the partitioner has at least one aperture extending from the first surface to its second surface, allowing passage of moisture through the thickness of the partitioner. The partitioner can connect to the rest of the container by a hinge, or, alternatively, it can be a separable lid that snaps onto the rest of the container.

Within the container, a support (e.g., a perforated plate) is received in the inner area, wherein the support distinguishes two spaces within the inner area: a space for supporting a liquid reservoir (e.g., wetting pad, sponge), and a space for holding free-flowing liquid. The support has a surface facing the bottom of the container, another surface on the opposite side to support and hold a commercially available liquid reservoir. Similar to the partitioner, the support has at least one through hole extending from its one surface to its other surface, allowing fluid communication of moisture and/or other liquid (e.g., water) therethrough. The portable container is designed to be placed inside the main housing of a wipe warmer, near or under where baby wipes are typically placed. This way, a typical heater in known wipe warmers can apply heat to the container, thereby releasing moisture from the container.

While the preferred embodiments have a support (e.g., a perforated support plate) that creates two separate spaces in a top-bottom arrangement, it is further contemplated that the the support can create other spatial arrangements that are not top-bottom. For example, in one contemplated embodiment, the support is placed in a vertical orientation, creating two spaces in a side-by-side arrangement.

In some preferred embodiments, the at least one through hole of the support and the at least one aperture of the partitioner are misaligned (or offset) with each other, such that one aperture is not directly located above one through hole. Of course, a mixture of aligned aperture-through hole with misaligned aperture-through hole is also contemplated.

There are many ways to keep the support in place. In some embodiments, the container uses at least one sustainer between the bottom of the container and the support for spacing the support apart from the bottom of the container.

In the preferred embodiments, the container is designed to provide an enclosure to hold free-flowing liquid and/or commercially known liquid reservoir (e.g., wetting pad, sponge). Therefore, the container has a lateral wall surrounding and in connection with the bottom, and the partitioner connects to the lateral wall of the container so as to form a portable case/container/basket separable and removable from the wipe-receiving area (e.g., a room) of the main housing. Contemplated container can or cannot have perforated bottom or perforated wall. In less preferred embodiments, the bottom and/or the walls of the container have openings allowing free-flowing liquid to flow in-and-out of the container, to and from the enclosed room-like space.

With the container placed inside the main housing, the wipe-receiving area is now defined by the second surface of the partitioner, the inner walls of the main housing cover, and walls of the room.

Another aspect of the inventive subject matter is directed to a wipe warmer having a perforated support plate and a perforated partitioner in place using sustainers built into the inner side walls of its wipe-receiving area, without the need for having separate/removable container. The goal is to have separated spaces for liquid reservoir and free-flowing liquid, yet allowing moisture to pass from one space to another space.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWINGS

It should be noted that the drawing figures may be in simplified form and might not be to precise scale. In reference to the disclosure herein, for purposes of convenience and clarity only, directional terms, such as, top, bottom, left, right, up, down, over, above, below, beneath, rear, front, distal, and proximal are used with respect to the accompanying drawings. Such directional terms should not be construed to limit the scope of the invention in any manner.

DETAILED DESCRIPTION OF THE INVENTION

The invention and its various embodiments can now be better understood by turning to the following detailed description of the preferred embodiments, which are presented as illustrated examples of the invention defined in the claims. It is expressly understood that the invention as defined by the claims may be broader than the illustrated embodiments described below.

Figure 1:
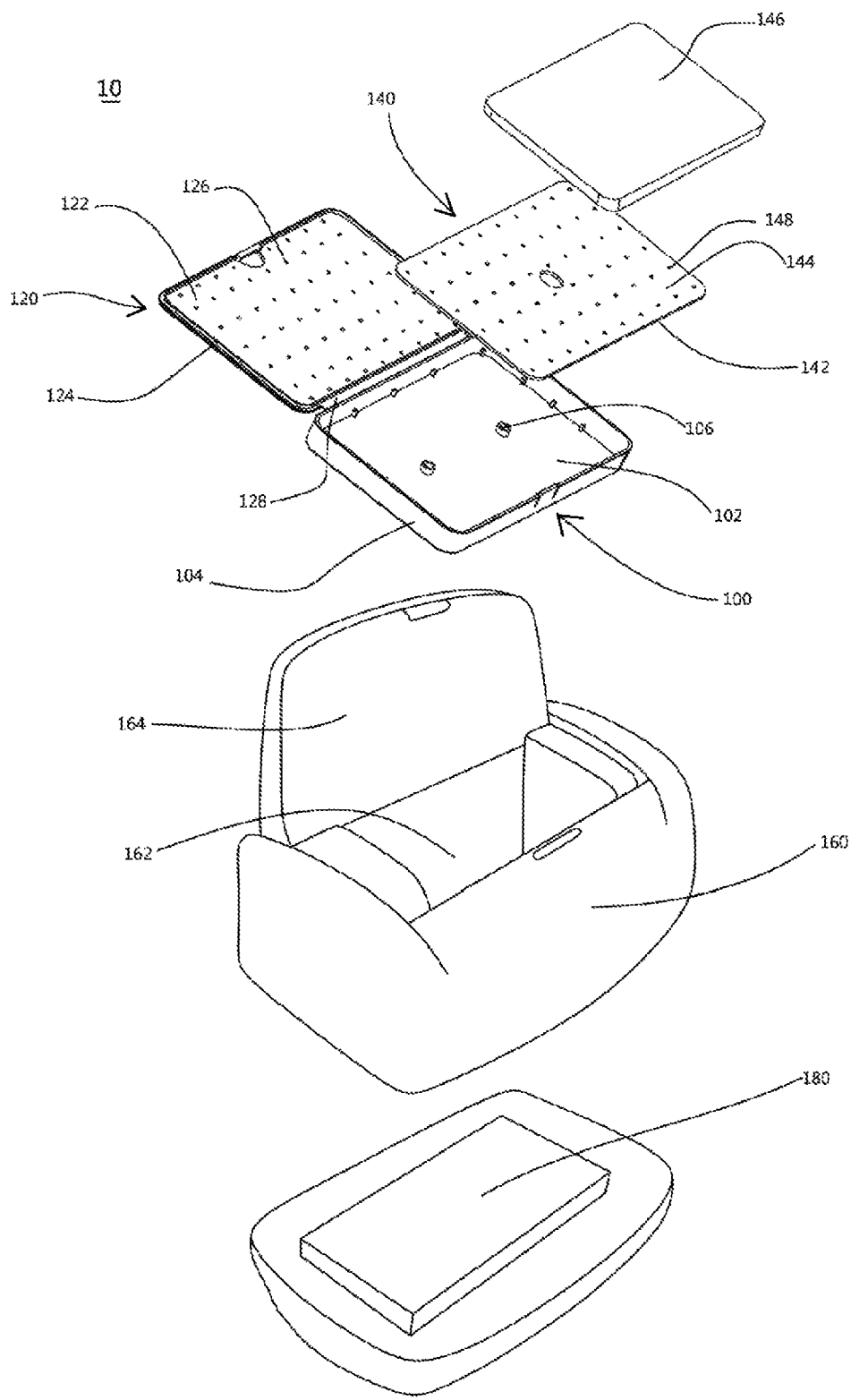
FIG. 1 is an exploded and perspective view of a first embodiment of a wipe warmer having humidifying device according to an aspect of the inventive subject matter.
Figure 2:
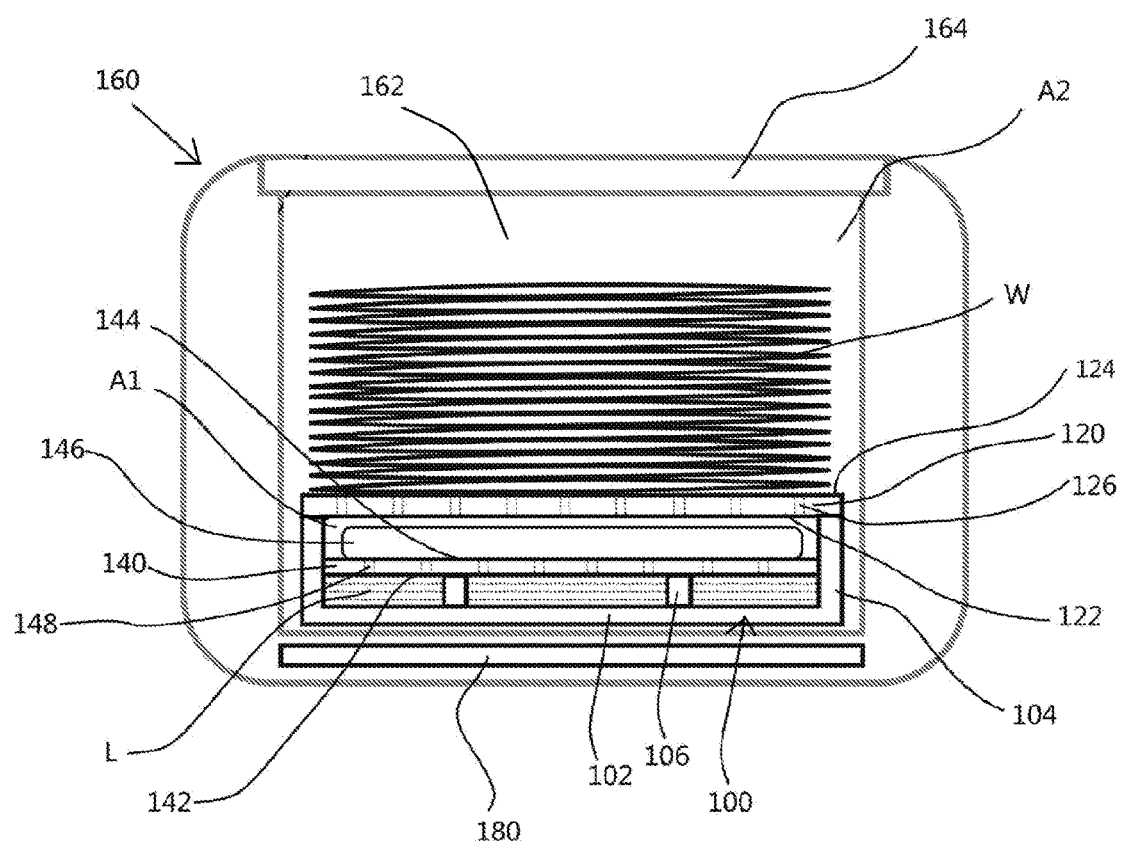
FIG. 2 is a cross-sectional view of the first embodiment of the wipe warmer having humidifying device of FIG. 1.

Referring to FIGS. 1 and 2, a wipe warmer 10 of a first embodiment of the inventive subject matter is shown. The wipe warmer 10 includes a container 100 for receiving liquid L inside; a partitioner 120 pivotably coupled with the container 100 to form an inner area A1 in the container 100; a support 140 received in the inner area A1; a main housing 160 to receive the container 100, and a heater 180 arranged in the bottom of the main housing 160 so as to heat the liquid L received in the container 100. Specifically, a combination of the container 100, partitioner 120, and support 140 can be further regarded as a humidifying device.

Specifically, the container 100 has a bottom 102 and a lateral wall 104 surrounding and in connection with the bottom 102 so as to contain the liquid L above the bottom 102 and within inner area A1, wherein the liquid L may be water to be heated to generate warm vapor. Warm vapor is to pass through the support 140 and partitioner 120 into the area surrounding the container 100. Optionally, there may be a sustainer 106 formed inside the inner area A1 and on the bottom 102 of the container 100, so as to uphold and separate the support 140 away from the bottom 102.

Here, the inner area A1 is an entirely closed space. Any moisture or liquid enclosed within area A1 may escape only through the plurality of apertures 126, when the partitioner 120 is closed shut on the container 100.

In some other embodiments not illustrated in the drawing figures, the inner area A1 is not entirely closed space, even when the partitioner 120 is closed shut. For example, in less preferred embodiments, the lateral wall 104, or the bottom 102, or both, can have openings or perforations, allowing moisture/liquid to freely pass in-and-out of the container 100.

In the illustrated embodiment shown in FIGS. 1 and 2, the partitioner 120 couples to the lateral wall 104 of the container 100 and jointly define the inner area A1 of the container 100. The partitioner 120 has a first surface 122 facing the inner area A1, a second surface 124 opposite to the first surface 122, and a plurality of apertures 126 extending from the first surface 122 to the second surface 124, allowing fluid communication of moisture and/or liquid between two sides of the partitioner 120. Particularly, the second surface 124 is adapted to face a wipe-receiving area A2 of the wipe warmer 10, wherein the wipe-receiving area A2 is to receive at least one wipe W in the wipe warmer 10. In this embodiment, said wipe-receiving area A2 is above the partitioner 120 when the wipe warmer 10 is in use, and when the at least one wipe W is piled on the second surface 124 of the partitioner 120. The apertures 126 penetrate through the thickness of the partitioner 120 from the first surface 122 to the second surface 124. As described above, the apertures 126 allows moisture to pass through the partitioner 120 from the inner area A1 to the wipe-receiving area A2, and vice versa. The idea is so that warm vapor generated in the inner area A1 can enter into the wipe-receiving area A2 via the apertures 126 to moisten wipes W. Preferably, the apertures 126 are positioned into an array. In other embodiments, the apertures 126 are equidistant to each other.

Various ways are contemplated for coupling the partitioner 120 to the container 100. For example, the partitioner 120 may be connected to the container 100 via a hinge 128. This way, the partitioner 120 serves as a pivoting cover of the container 100. In other embodiments, the partitioner 120 can be a snap-on lid. One skilled in the art would immediately recognize other typical ways to use and couple the partitioner 120 as a lid to the container 100. In most preferred embodiments, a combination of the container 100 and the partitioner 120 forms a portable case separable and removable from the wipe-receiving area A2.

The support 140 received in the inner area A1 has a third surface 142 facing the bottom 102 of the container 100, a fourth surface 144 opposite to the third surface 142 to support a liquid reservoir 146, such as a sponge. In the preferred embodiment, the support 140 has a plurality of through holes 148 extending from the third surface 142 to the fourth surface 144. Preferably, the through holes 148 are also positioned into an array. Even more preferably the through holes 148 are equidistant to each other.

While support 140 in all of the illustrated drawings is shown to have through holes 148, less preferred embodiments of the inventive subject matter can have no through holes at all, so long as there is left some kind of passage for moisture to pass from the bottom side of the support to the upper side of the support 140. For example, a gap can be provided between the support 140 and the surrounding lateral walls 104.

Returning now to FIG. 2, the through holes 148 are also adapted for warm vapor originating from the liquid L to pass through, so as to moisten the liquid reservoir 146. Warm vapor can further enter into the wipe-receiving area A2 via apertures 126. Also specifically contemplated are many ways to use the container 100 as shown in FIG. 2. In one method, the liquid reservoir 146 is disposed by a user between the fourth surface 144 of support 140 and the first surface 122 of the partitioner 120. That is, the liquid reservoir 146 may be disposed above the support 140 (as shown in FIG. 2). In another method, the liquid reservoir 146 may be disposed below the support 140 (not shown). In either method, a user may add various volumes of free-flowing liquid (e.g., water) into the container 100. For example, the liquid can be no higher than the support 140. In another example, the liquid can overwhelm the support 140.

Contemplated main housing 160 has a room 162 for receiving the portable case/container 100 having the partitioner 120. In this first embodiment, a part of the inner space of the room 162 is for positioning the portable container 100, and another part of the inner space of the room 162 serves as the wipe-receiving area A2 to store wipes W. As is known in the art, the main housing 160 has a cover 164 capable of sealing the room 162, so that warm vapor in the wipe-receiving area A2 can be kept within the room 162 to keep the wipes W moistened. Namely, in this embodiment, the wipe-receiving area A2 is defined by the second surface 124 of the partitioner 120 and inner walls of the room 162 and cover 164.

As is known in the art, the heater 180 is arranged in the main housing 160, usually at the bottom 102 of the main housing 160 to heat the room 162. In the contemplated embodiments, the heater 180 is also arranged at the bottom 102 of the main housing to heat liquid L in the container 100.

The heater 180 may be located in other parts of the main housing 160, so long as it is adjacent to the desired location of the container 100. As will be seen in FIG. 3, a desired location of the container 100 may be to the side of the room 162. In such embodiments, the heater 180 can be disposed underneath the container location, or on the side wall adjacent to the container location. In further contemplated embodiments (not shown), the heater 180 can even be placed near the top of the room 162, for example, in the cover 164 of the main housing 160, so as to heat container 100 located somewhere near the cover 164. In this design, heat is applied in a direction from top of the room 162 towards the bottom of the room 162.

In practical use of this wipe warmer 10, the wipes W are disposed on the second surface 124 of the partitioner 120 as described previously, and then warm vapor is created by heating the liquid L in the container 100. The warm vapor goes upwards via the through holes 148 of the support 140 to moisten the liquid reservoir 146, so that the wet liquid reservoir 146 can serve as a thermal buffer. Finally, the wet vapor further goes upwards to the wipes W in the wipe-receiving area A2 by first passing through the apertures 126 of the partitioner 120. Specifically, the moistened liquid reservoir 146 arranged between the wipes W and the heater 180 prolongs the moistened state of the wipes W, and works better than having only a pool of heated water alone, or having only a moistened or soaked liquid reservoir alone. Furthermore, another key discovery of the inventive subject matter is the advantage of disposing the liquid reservoir 146 spaced apart from the heater 180 by at least the support 140 and the bottom 102 of the container 100, allowing gradual and indirect heating via a pool of water. This arrangement surprisingly and advantageously prolongs the moistening effect and usable life of the liquid reservoir 146.

Figure 3:
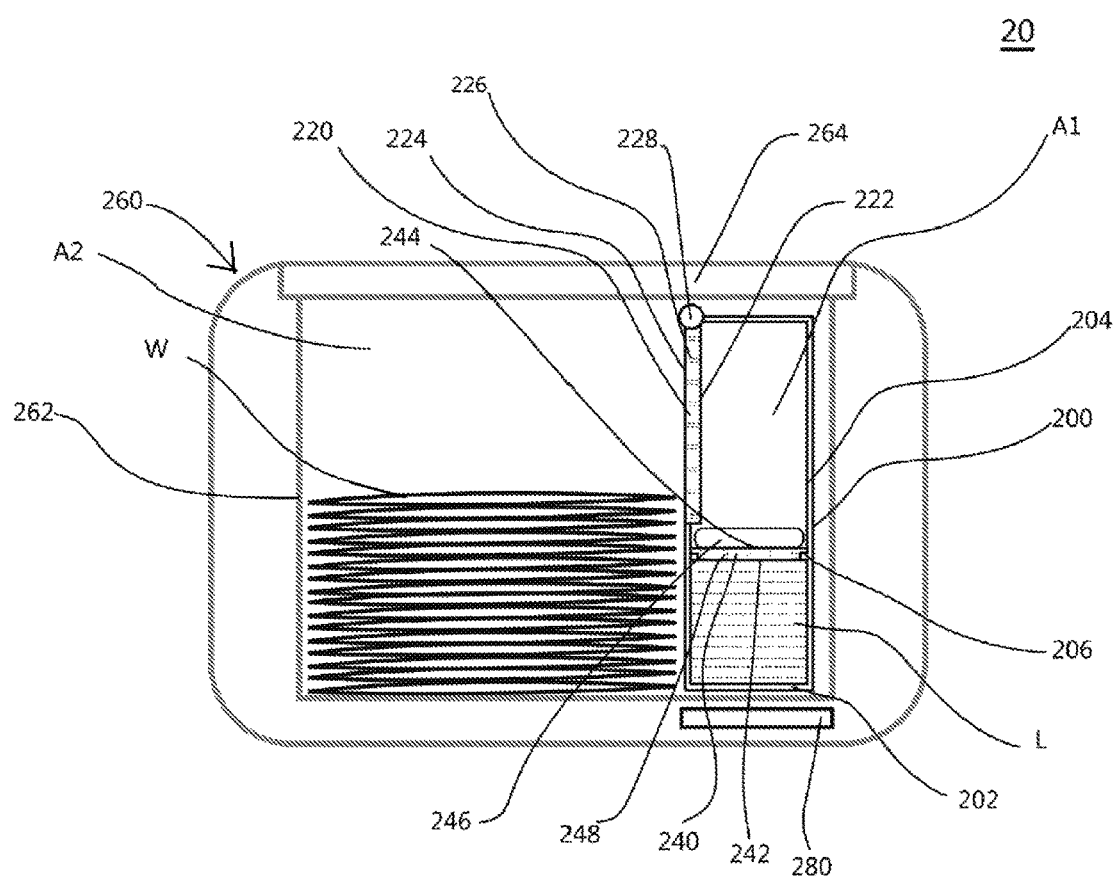
FIG. 3 is a cross-sectional view of a second embodiment of a wipe warmer having humidifying device according to an aspect of the inventive subject matter.

Please refer now to FIG. 3, which shows a wipe warmer 20 of a second embodiment having a container 200 for receiving liquid L inside, a partitioner 220 coupled with the container 200 to form an inner area A1 in the container 200, a support 240 received in the inner area A1, a main housing 260 having a room for receiving the container 200 towards one side of the room instead of at the bottom of the room, and a heater 280 arranged in the main housing 260 directly beneath the container 200 so as apply heat to the liquid L in the container 200. Comparing to the wipe warmer 10 of the first embodiment, here, wipes W and container 200 are arranged side-by-side in the room 262, and the container 200 does not serve as a tray to hold at wipes W.

In the embodiment as shown in FIG. 3, the container 200 has a bottom 202 and a lateral wall 204 surrounding and in connection with the bottom 202 so as to contain liquid L above the bottom 202. A sustainer 206 is formed inside an inner area A1 and on an inner side of the lateral wall 204, so as to support and separate the support 240 from the bottom 202. The support 240 is disposed horizontally flat. Alternatively, in order to space the support 240 apart and away from the bottom 202, instead of forming the sustainer 206, an inner surface of the lateral wall 204 may be inclined (not shown) relatively to the bottom 202, so that the inner surface of the lateral wall 204 is tapered from an upper opening of the container 200 to the bottom 202, and the support 240 directly abuts against the inner surface of the lateral wall 204.

The partitioner 220 has a first surface 222 facing the inner area A1, a second surface 224 opposite to the first surface 222, and a plurality of apertures 226 extending from the first surface 222 to the second surface 224. Particularly, the second surface 224 is adapted to face a wipe-receiving area A2 of the wipe warmer 20, wherein the wipe-receiving area A2 is for receiving at least one wipe W in the wipe warmer 20. In this embodiment, instead of being piled on the second surface 224, said wipe-receiving area A2 is piled besides the partitioner 220 when the wipe warmer 20 is in use. The apertures 226, penetrating through the thickness of the partitioner 220 from the first surface 222 to the second surface 224, allow fluid communication between the inner area A1 and the wipe-receiving area A2 for the warm vapor originated from the heated liquid L. Preferably, the apertures 226 are positioned into an array. Preferably, the partitioner 220 connects to the container 200 via a hinge 228, and thus the partitioner 220 may serve as a cover of the container 200, so that a combination of the container 200 and the partitioner 220 forms a portable case separable from the wipe-receiving area A2.

The support 240 received in the inner area A1 includes a third surface 242 facing the bottom 202 of the container 200, a fourth surface 244 opposite to the third surface 242 and supporting a liquid reservoir 246, and a plurality of through holes 248 extending from the third surface 242 to the fourth surface 244. Preferably, the through holes 248 are also positioned into an array.

The main housing 260 has a room 262 for receiving the portable case formed by the container 200 and the partitioner 220. In this second embodiment, a part of the inner space of the room 262 is for positioning the portable case, and the another part of the inner space of the room 262 serves as the wipe-receiving area A2 having wipes W. Furthermore, the main housing 260 may also include a cover 264 capable of sealing the room 262, so as to keep the warm vapor ejected into the wipe-receiving area A2 in the room 262. Namely, in this embodiment, the wipe-receiving area A2 is defined by the second surface 224 of the partitioner 220 and inner walls of the room 262 and cover 264.

Figure 4:
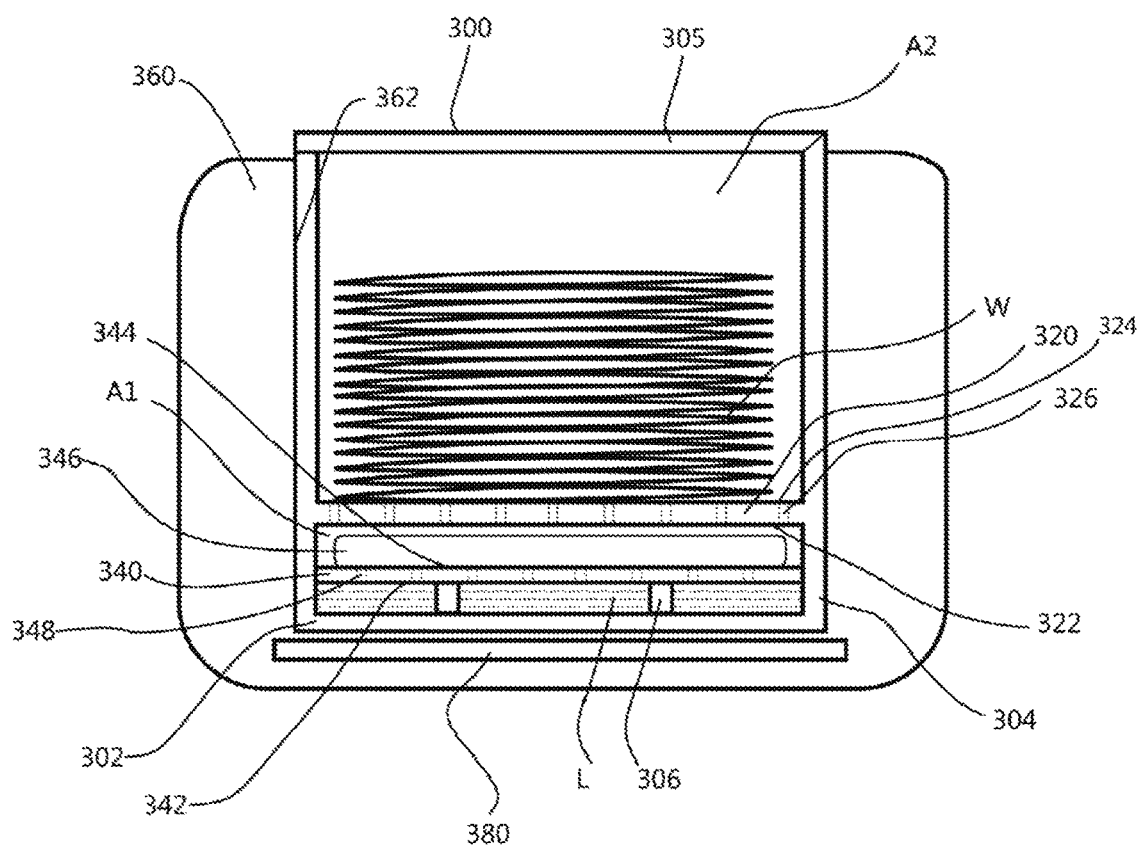
FIG. 4 is a cross-sectional view of a third embodiment of a wipe warmer having humidifying device according to an aspect of the inventive subject matter.

FIG. 4 shows a wipe warmer 30 of a third embodiment of the inventive subject matter. The wipe warmer 30 also includes a container 300 for receiving liquid L inside, a partitioner 320 coupled with the container 300 to form an inner area A1 in the container 300, a support 340 received in the inner area A1, a main housing 360 coupled with the container 300, and a heater 380 arranged in the main housing 360 so as to heat the liquid L received in the container 300. In comparison with previous illustrated wipe warmers 10, 20, however, instead of being beneath or beside the wipes W, the humidifying device of the wipe warmer 30 receives the wipes W inside the container 300.

Specifically, the container 300 has a bottom 302 and a lateral wall 304 surrounding and in connection with the bottom 302 so as to contain the liquid L above the bottom 302. The lateral wall 304 extends not only towards but also over the partitioner 320. Moreover, the container 300 has a cover 305 opposite to the bottom 302, so as to jointly define a wipe-receiving area A2 inside the container 300 with the lateral wall 304, the cover 305 and the partitioner 320. The wipe-receiving area A2 receives wipes W. Specifically, the cover 305 is adapted to seal the container 300, so that warm vapor sourced from the heated liquid L can be kept in the wipe-receiving area A2. There may be a sustainer 306 formed inside the inner area A1 and on the bottom 302 of the container 300, so as to uphold and separate the support 340 away from the bottom 302 in a vertical direction.

The partitioner 320 couples with the lateral wall 304 of the container 300 and jointly defines the inner area A1. Partitioner 320 has a first surface 322 facing the inner area A1, a second surface 324 opposite to the first surface 322, and a plurality of apertures 326 extending from the first surface 322 to the second surface 324. Particularly, the second surface 324 is adapted to face the wipe-receiving area A2. In other words, said wipe-receiving area A2 of this embodiment is defined by the second surface 324 and the lateral wall 304 and cover 305 of the container 300. The apertures 326, penetrate through the thickness of the partitioner 320 from the first surface 322 to the second surface 324, allows fluid communication between the inner area A1 and the wipe-receiving area A2 for warm vapor originated from the heated liquid L. Similarly to other embodiments, the apertures 326 are positioned into an array.

The support 340 received in the inner area A1 includes a third surface 342 facing the bottom 302 of the container 300, a fourth surface 344 opposite to the third surface 342 and supporting a liquid reservoir 346, such as a sponge or a wetting pad, and a plurality of through holes 348 extending from the third surface 342 to the fourth surface 344. Preferably, the through holes 348 are also positioned into an array. Preferably, the through holes 348 misalign with the apertures 326 of the partitioner 320 in the vertical direction such at an aperture 326 is not directly above a through hole 348. In one embodiment, support 340 can be entirely removed from the container 300.

The main housing 360 may have a room 362 for receiving the container 300. However, the main housing 360 may also be a seat for merely supporting the container 300. The heater 380 is arranged in the main housing 360, which is adjacent to the bottom 302 of the container 300 and adapted to heat the liquid L therein. Specifically, the heater 380 is imbedded in the main housing 360 and outside the room 362 in this embodiment.

In this third embodiment, both of the inner area A1 and wipe-receiving area A2 are inside the container 300, which are separated by the partitioner 320, and thus electrical parts of the wipe warmer 30 for operation of the heater 380 can be totally removed from both of these areas A1, A2 as long as the container 300 is disengaged with and away from the main housing 360. Therefore, the user can clean the container 300 and elements inside areas A1, A2 by water without danger of electrical shock or water damage to electrical parts, thereby improving product safety.

Figure 5:
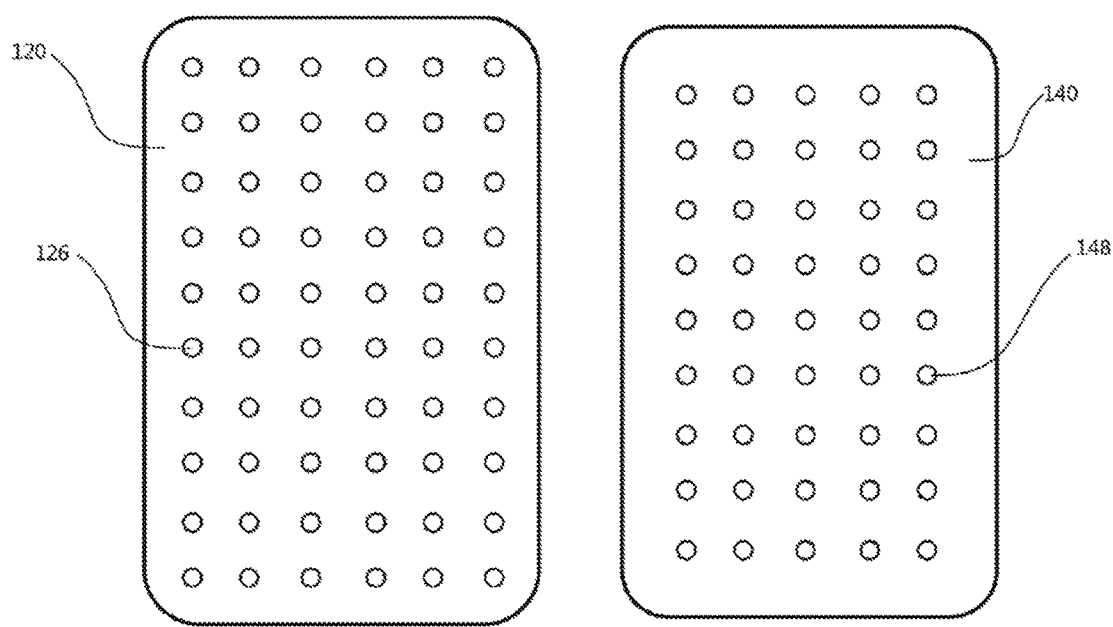
FIG. 5 is a top view of a partitioner having a plurality of apertures, juxtaposed to a support having a plurality of through holes, according to an aspect of the inventive subject matter.
Figure 6:
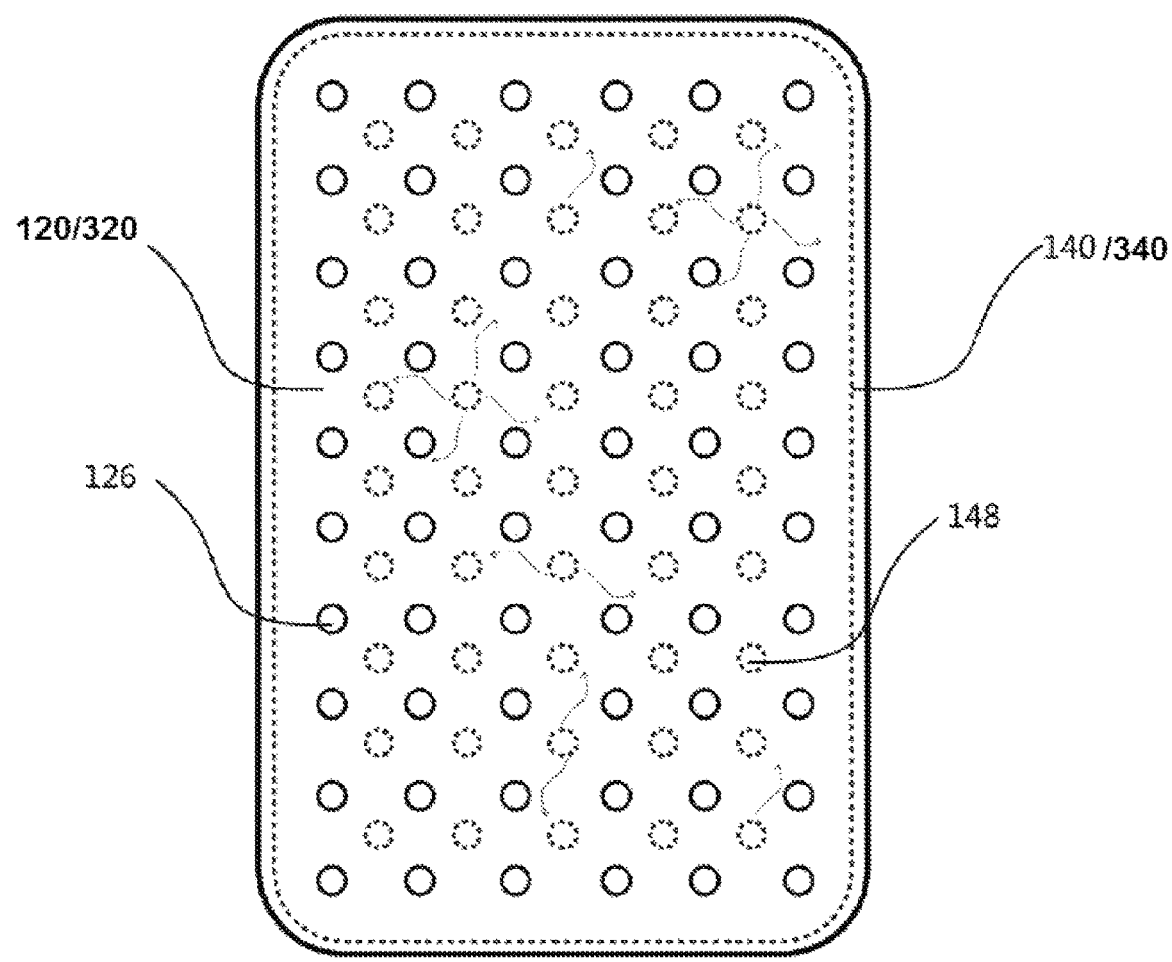
FIG. 6 is a top view of the partitioner and support of FIG. 5, wherein the partitioner is placed directly on top of the support, showing misalignment of apertures and through holes, according to an aspect of the inventive subject matter.

Referring now to FIG. 5 and FIG. 6, both of which illustrate the inventive concept of misaligning/offsetting apertures and through holes to achieve desirable moistening of liquid reservoir 146. FIG. 5 is a top view of a partitioner 120, and a top view of a support 140. FIG. 6 is a top view of the partitioner 120, 320 placed over the support 140, 340 as shown in embodiments illustrated in FIGS. 2 and 4. Here, moisture passing through through hole 148 travels next in a lateral direction in order to reach the closest aperture 126, thereby moistening a much larger portion of liquid reservoir 146, versus where apertures and through holes are vertically aligned.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed herein even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims therefore include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Thus, specific embodiments and applications of wipe warmer have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention.

What is claimed is:

1. A humidifying device sized to fit within a baby wipe warmer, comprising:
   a container having a bottom and adapted to receive liquid above the bottom;
   a partitioner coupled with the container to form an inner area in the container, wherein the partitioner has a first surface facing the inner area, a second surface opposite to the first surface, and at least one aperture extending from the first surface to the second surface;
   a movable support received in the inner area, wherein the movable support has a third surface facing the bottom of the container, a fourth surface opposite to the third surface, and a through hole extending from the third surface to the fourth surface and communicating with the at least one aperture of the partitioner;
   a wetting pad having a bottom surface dimension, the wetting pad is disposed on the third surface;
   wherein the third surface has a surface dimension substantially equal to the bottom surface dimension of the wetting pad; and
   a sustainer between the bottom of the container and the third surface of the movable support for spacing the bottom and the third surface.

2. The humidifying device as claimed in claim 1, wherein the third surface of the movable support is spaced from the bottom of the container in a vertical direction.

3. The humidifying device as claimed in claim 2, wherein the through hole of the movable support and the aperture of the partitioner are misaligned with each other in the vertical direction.

4. The humidifying device as claimed in claim 1, wherein the partitioner connects with the container by a hinge.

5. The humidifying device as claimed in claim 1, wherein the partitioner has a plurality of apertures extending from the first surface to the second surface, and all of the plurality of apertures are positioned into an array.

6. The humidifying device as claimed in claim 1, wherein the movable support further has other through holes extending from the third surface to the fourth surface, and all of the through holes are positioned into an array.

7. The humidifying device as claimed in claim 1, wherein the partitioner further has other apertures extending from the first surface to the second surface, the movable support further has other through holes extending from the third surface to the fourth surface, the third surface of the movable support is spaced from the bottom of the container in a vertical direction, and all of the through holes of the movable support misalign with all of the apertures of the partitioner in the vertical direction.

8. The humidifying device as claimed in claim 1, wherein the first surface of the partitioner faces the bottom of the container, and the second surface of the partitioner is positioned directly above the bottom of the container.

9. The humidifying device as claimed in claim 1, wherein the third surface of the movable support is spaced from the bottom of the container, the container has a lateral wall surrounding and in connection with the bottom, and the partitioner connects with the lateral wall of the container so that a combination of the container and the partitioner forms a portable case.

10. The humidifying device as claimed in claim 1, wherein the container has a lateral wall surrounding and in connection with the bottom, wherein the partitioner forms part of the lateral wall.

11. A wipe warmer, comprising:
    a container having a bottom and adapted to receive liquid above the bottom;
    a partitioner coupled with the container to form an inner area in the container, wherein the partitioner has a first surface facing the inner area, a second surface opposite to the first surface, and an aperture extending from the first surface to the second surface;
    a movable support received in the inner area, wherein the movable support has a third surface facing the bottom of the container, a fourth surface opposite to the third surface, and a through hole extending from the third surface to the fourth surface and communicating with the aperture of the partitioner;
    a main housing coupled with the container;
    a heater arranged in the main housing and adjacent to the bottom of the container, wherein the heater is adapted to heat the liquid in the container;
    a wetting pad having a bottom surface dimension, the wetting pad is disposed on the third surface;
    wherein the third surface has a surface dimension substantially equal to the bottom surface dimension of the wetting pad; and
    a sustainer between the bottom of the container and the third surface of the movable support for spacing the bottom and the third surface.

12. The wipe warmer as claimed in claim 11, wherein the third surface of the movable support is spaced from the bottom of the container in a vertical direction, and the through hole of the movable support and the aperture of the partitioner are misaligned with each other in the vertical direction.

13. The wipe warmer as claimed in claim 11, wherein the first surface of the partitioner faces the bottom of the container, and the second surface of the partitioner is further adapted to movable support the at least one wipe.

14. The wipe warmer as claimed in claim 11, wherein the third surface of the movable support is spaced from the bottom of the container, the container has a lateral wall surrounding and in connection with the bottom, and the partitioner connects with the lateral wall of the container so that a combination of the container and the partitioner forms a portable case.

15. The wipe warmer as claimed in claim 14, wherein the main housing has a room receiving the portable case and a cover sealing the room, and the wipe-receiving area is defined by the second surface of the partitioner and inner walls of the cover and the room.

16. The wipe warmer as claimed in claim 15, wherein the third surface of the movable support is spaced from the bottom of the container in a vertical direction, and the through hole of the movable support and the aperture of the partitioner are misaligned with each other in the vertical direction.

17. The wipe warmer as claimed in claim 16, wherein the partitioner further comprises a plurality of apertures extending from the first surface to the second surface, the movable support further has a plurality of through holes extending from the third surface to the fourth surface, and the plurality of through holes of the movable support misalign with the plurality of apertures of the partitioner in the vertical direction.

18. The wipe warmer as claimed in claim 11, wherein the container has a lateral wall surrounding and in connection with the bottom, wherein the partitioner forms part of the lateral wall.

* * * * *